United States Patent
Yamada et al.

(10) Patent No.: US 10,563,238 B2
(45) Date of Patent: Feb. 18, 2020

(54) METHOD OF PRODUCING A SUGAR LIQUID

(71) Applicant: Toray Industries, Inc., Tokyo (JP)

(72) Inventors: Chiaki Yamada, Kamakura (JP); Hiroyuki Kurihara, Kamakura (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 911 days.

(21) Appl. No.: 14/913,404

(22) PCT Filed: Aug. 21, 2014

(86) PCT No.: PCT/JP2014/071911
§ 371 (c)(1),
(2) Date: Feb. 22, 2016

(87) PCT Pub. No.: WO2015/025927
PCT Pub. Date: Feb. 26, 2015

(65) Prior Publication Data
US 2016/0208300 A1    Jul. 21, 2016

(30) Foreign Application Priority Data

Aug. 22, 2013 (JP) ................................. 2013-172186

(51) Int. Cl.
*C12P 19/02* (2006.01)
*C12P 7/56* (2006.01)
*C12P 19/14* (2006.01)

(52) U.S. Cl.
CPC .............. *C12P 19/02* (2013.01); *C12P 7/56* (2013.01); *C12P 19/14* (2013.01); *C12P 2201/00* (2013.01); *C12P 2203/00* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 2009/0050134 A1 | 2/2009 | Friend et al. | |
| 2011/0079219 A1* | 4/2011 | McDonald | C13K 1/02 127/1 |
| 2012/0052536 A1 | 3/2012 | Medoff et al. | |
| 2013/0203117 A1* | 8/2013 | Kurihara | C12P 19/14 435/72 |

FOREIGN PATENT DOCUMENTS

| | | |
|---|---|---|
| CN | 102791874 A | 11/2012 |
| JP | 63-087994 A | 4/1988 |
| JP | 01-312997 A | 12/1989 |
| JP | 2010-536558 A | 12/2010 |
| JP | 2012-100617 A | 5/2012 |
| JP | 4947223 B1 | 6/2012 |
| JP | 2013-530724 A | 8/2013 |
| WO | 2010/067785 A1 | 6/2010 |
| WO | 2011/115040 A1 | 9/2011 |

OTHER PUBLICATIONS

Lu, Yanpin, et al. "Cellulase adsorption and an evaluation of enzyme recycle during hydrolysis of steam-exploded softwood residues." Applied biochemistry and biotechnology 98.1-9 (2002): 641-654. (Year: 2002).*
Li, Ping, et al. "Effect of acid pretreatment on different parts of corn stalk for second generation ethanol production." Bioresource technology 206 (2016): 86-92. (Year: 2016).*
The First Office Action dated Jul. 5, 2018, of counterpart Chinese Application No. 201480046133.0, along with an English translation.
D.E. Otter et al., "Elution of *Trichoderma reesei* Cellulase From Cellulose by pH Adjustment With Sodium Hydroxide," Biotechnology Letters, vol. 6, No. 6 (1984), pp. 369-374.
Notice of Reasons for Refusal dated Sep. 14, 2018, of counterpart Japanese Application No. 2014-552414, including an English translation.

* cited by examiner

*Primary Examiner* — Robert J Yamasaki
(74) *Attorney, Agent, or Firm* — DLA Piper LLP (US)

(57) ABSTRACT

A method of producing a sugar liquid includes steps (1) providing a pretreatment product of a first cellulose-containing biomass; (2) adding a second cellulose-containing biomass or a pretreatment product thereof in an amount ranging from 1 to 50% based on the solid content weight of the first cellulose-containing biomass pretreatment product of step (1), and carrying out hydrolysis by a filamentous fungus-derived cellulase; and (3) subjecting a hydrolysate of step (2) to solid-liquid separation to obtain a solution component and a hydrolysis residue, and filtering the solution component through an ultrafiltration membrane to recover the filamentous fungus-derived cellulase as a retentate and recover a sugar liquid as a permeate.

16 Claims, 1 Drawing Sheet

METHOD OF PRODUCING A SUGAR LIQUID

TECHNICAL FIELD

This disclosure relates to methods of producing a sugar liquid from cellulose.

BACKGROUND

Due to less energy consumption and less environmental impact, as well as more sugar yield, methods of hydrolyzing biomass by using cellulase have been widely studied. However, there is a drawback in such a method of hydrolyzing biomass by using cellulase in that the cost of sugar liquid production increases due to the high price of cellulase. To solve such a technological problem, methods of recovering to reuse cellulase used in the hydrolysis have been suggested. Nonetheless, the cellulase is strongly adsorbed by hydrolysis residues generated when cellulose-containing biomass is hydrolyzed and therefore enzyme's reusability is low, which has been problematic.

As for methods of desorbing the cellulase adsorbed by the hydrolysis residue to increase the recovery of cellulase, disclosed are a method of washing hydrolysis residues with an aqueous sodium hydroxide solution of about pH 8 (D. E. Otter et al., "Elution of *Trichoderma reesei* Cellulase from Cellulose by pH Adjustment with Sodium Hydroxide," Biotechnology Letters (1984), Vol. 6, No. 6, 369-374), a method of bringing hydrolysis residues into contact with a nonionic surfactant (Japanese Patent Application Laid-Open Publication No. S63-87994), and the like. Meanwhile, as for methods of decreasing the adsorption of cellulase to hydrolysis residues, known are a method of adding water-soluble salts at the time of the hydrolysis of cellulose-containing biomass to adjust an electrical conductivity to 5 to 25 mS/cm (Japanese Patent No. 4947223), a method of adding calcium carbonate particles in 1 to 10% by weight based on the solid weight of cellulose-containing biomass (Japanese Patent Application Laid-Open Publication No. 2012-100617) and the like.

As mentioned above, various attempts have been made to reduce cellulase consumption by recovering and reusing the cellulase used for the hydrolysis of cellulose-containing biomass. But, the problem has not been solved because the cellulase is strongly adsorbed by hydrolysis residues and the recovery is thus low.

It could therefore be helpful to provide methods of producing a sugar liquid capable of more effectively reduce the cellulase consumption than conventional methods.

SUMMARY

We found that, when a pretreatment product of the first cellulose-containing biomass is hydrolyzed by filamentous fungus-derived cellulase, addition of the second cellulose-containing biomass or a pretreatment product thereof in an amount ranging from 1 to 50% based on the solid content weight of the above-mentioned pretreatment product makes it possible to recover enzyme components of the filamentous fungus-derived cellulase at a significantly high efficiency.

We thus provide:

[1] A method of producing a sugar liquid comprising the following steps (1) to (3):
  Step (1): the step of providing a pretreatment product of a first cellulose-containing biomass,
  Step (2): the step of adding a second cellulose-containing biomass or a pretreatment product thereof in an amount ranging from 1 to 50% based on the solid content weight of the first cellulose-containing biomass pretreatment product of step (1), and of carrying out hydrolysis by a filamentous fungus-derived cellulase, and
  Step (3): the step of subjecting a hydrolysate of step (2) to solid-liquid separation to obtain a solution component and a hydrolysis residue, and of filtering the solution component through an ultrafiltration membrane to recover the filamentous fungus-derived cellulase as a retentate and to recover a sugar liquid as a permeate.

[2] The method of producing a sugar liquid according to [1], wherein the pretreatment product of the second cellulose-containing biomass of step (2) is a pretreatment product obtained by subjecting the second cellulose-containing biomass to a hydrothermal treatment and/or an acid treatment.

[3] The method of producing a sugar liquid according to [1] or [2], wherein the second cellulose-containing biomass of step (2) is a grain hull.

[4] The method of producing a sugar liquid according to any of [1] to [3], wherein the second cellulose-containing biomass of step (2) is one or more biomasses selected from the group consisting of a corn hull, a soybean hull, and a wheat hull.

[5] The method of producing a sugar liquid according to any of [1] to [4], wherein the first cellulose-containing biomass of step (1) is an herbaceous biomass or a woody biomass.

[6] The method of producing a sugar liquid according to any of [1] to [5], wherein the first cellulose-containing biomass of step (1) is one or more biomasses selected from the group consisting of corn stover, a corncob, rice straw, wheat straw, barley straw, and bagasse.

[7] The method of producing a sugar liquid according to any of [1] to [6], wherein the pretreatment product of the first cellulose-containing biomass of step (1) is one pretreated by one or more methods selected from the group consisting of an acid treatment, an alkali treatment, a hydrothermal treatment, a subcritical water treatment, a pulverizing treatment, and a steaming treatment.

[8] A method of producing a chemical substance comprising the step of producing a sugar liquid by the method of producing a sugar liquid according to any of [1] to [7], and the step of culturing a microorganism using the sugar liquid obtained in the step of producing the sugar liquid as a fermentation raw material.

It is possible to inhibit adsorption of the filamentous fungus-derived cellulase to the hydrolysis residue of the cellulose-containing biomass and recover and/or reuse, at a high efficiency, a group of enzymes including cellobiohydrolase, endoglucanase, β-glucosidase, xylanase, and β-xylosidase, which play an important role in particular in a hydrolysis reaction. As a result, it is possible to reduce cellulase consumption when compared to the conventional methods, and thus to curb the costs of sugar liquid production.

DETAILED DESCRIPTION

Figure 1:
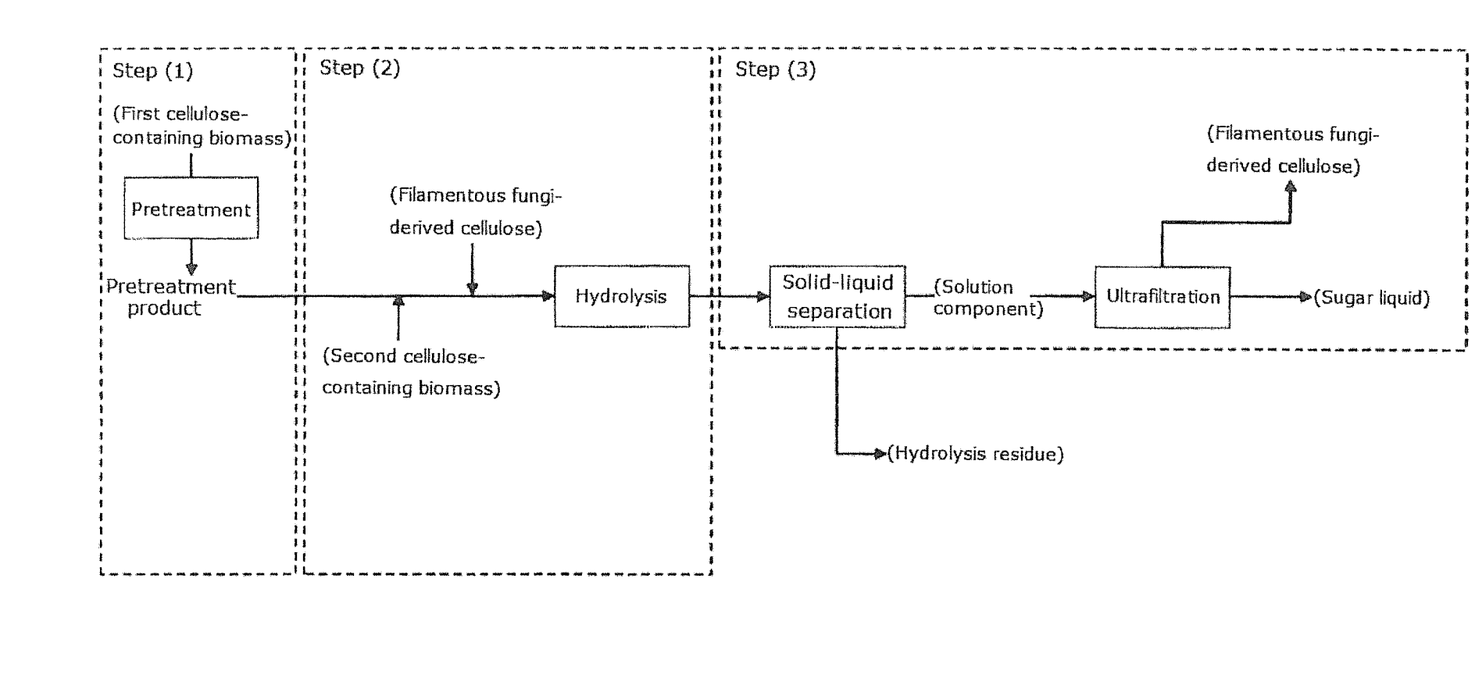
FIG. 1 is a schematic illustration showing one example carrying out the method of producing a sugar liquid.

Each of the steps of our methods will be individually described below.

Step (1): Providing a Pretreatment Product of the First Cellulose-Containing Biomass The first cellulose-containing biomass refers to bioresources that contain a cellulose component. The first cellulose-containing biomass is not particularly restricted; and specific examples thereof include herbaceous biomass such as bagasse, switchgrass, napier grass, Erianthus, corn stover, corncob, beet pulp, rice straw, wheat straw or barley straw; woody biomass such as trees and shrubs or waste building material; and biomass derived from aquatic environment such as algae or seagrass. Preferred specific examples thereof include herbaceous biomass or woody biomass, more preferred specific examples thereof include herbaceous biomass, and still more preferred specific examples thereof include one or more types selected from the group consisting of corn stover, corncob, rice straw, wheat straw, barley straw and bagasse.

The cellulose-containing biomass contains, in addition to cellulose and hemicellulose (hereinafter, the term "cellulose" is used as a general term of cellulose and hemicellulose), aromatic polymers such as lignins, and therefore the hydrolysis efficiency by cellulase can be improved by carrying out pretreatment. Examples of a pretreatment method include an acid treatment by sulfuric acid, acetic acid or the like, an alkali treatment by sodium hydroxide, ammonia or the like, a hydrothermal treatment, subcritical water treatment, pulverizing treatment, steaming treatment. What is effective are an ammonia treatment, a hydrothermal treatment, an acetic acid treatment, and a dilute sulfuric acid treatment; and thus these pretreatment methods are preferred. Biomass that has been subjected to the pretreatment is referred to as a biomass pretreatment product. The first cellulose-containing biomass may be preferably pretreated in provision for step (1). However, in preparation for step (1), the biomass pretreatment product that has been in advance subjected to pretreatment as described above may be purchased.

Besides solids derived from the cellulose-containing biomass, solution components containing xylose are contained in the pretreatment product of the cellulose-containing biomass, which solution components are generated by hydrolyzing part of hemicellulose contained in the cellulose-containing biomass. The pretreatment product refers to the product both in a state in which both of the solid residue and the solution component are included and in a state in which the solution component containing xylose is removed by solid-liquid separation and/or washing of the solid.

Step (2): the step of adding the second cellulose-containing biomass or a pretreatment product thereof in an amount of 1 to 50% based on the solid content weight of the pretreatment product of the first cellulose-containing biomass of step (1) to carry out hydrolysis by filamentous fungus-derived cellulase The second cellulose-containing biomass or a pretreatment product thereof is added when the first cellulose-containing biomass pretreatment product is hydrolyzed. The second cellulose-containing biomass, like the first cellulose-containing biomass, refers to bioresources that contain a cellulose component. Yet, it is characterized in that its plant species or plant parts are different from those of the first cellulose-containing biomass.

Preferred specific examples of the second cellulose-containing biomass include grain hulls. Grains refer to nuts and seeds based mainly on starch including Poaceae crops, Fabaceae crops, other plant nuts and seeds; and specific examples thereof can include corn, rice plant, barley and wheat, soybean, buckwheat soba, *Amaranthus*, and quinoa. All of these grains correspond to a nut-and-seed part whereas the grain hull refers to the outermost epidermis part of the nuts and seeds. For example, with regard to corn, wheat, soybean, and rice plant, the grain hull part may be removed in the process of food processing. This corresponds to production of starch with regard to corn, production of wheat flour with regard to wheat, production of soy bean oil with regard to soybean, the process of rice polishing, wherein polished rice is an edible part, with regard to rice plants. Such grain hulls contain cellulose and can therefore be said to be a cellulose-containing biomass generated in the abovementioned process of grain processing. The most preferred second cellulose-containing biomass is corn hulls, soybean hulls, and wheat hulls.

Although the second cellulose-containing biomass as is exerts sufficient effects, the pretreatment product obtained by subjecting the second cellulose-containing biomass to a hydrothermal treatment and/or an acid treatment is preferred. The pretreatment of the second cellulose-containing biomass can increase efficiency in breakdown of the second cellulose-containing biomass by a filamentous fungus-derived cellulase and can concurrently increase the amount of filamentous fungus-derived cellulase recovered in step (3).

The second cellulose-containing biomass is added in an amount ranging from 1 to 50% based on the solid content weight of the pretreatment product of the first cellulose-containing biomass of step (1). The solid content weight, when used herein, refers to a weight after the pretreatment product of the first cellulose-containing biomass and/or the second cellulose-containing biomass or the pretreatment product thereof are/is dried at 105° C. The solid concentration of the pretreatment product of the first cellulose-containing biomass and the second cellulose-containing biomass or the pretreatment product thereof can be calculated backwards by measuring the water content using a moisture meter with a heating drying mass measurement system. For example, when the water content of the pretreatment product of the first cellulose-containing biomass is 70% and the water content of the second cellulose-containing biomass or the pretreatment product thereof is 10%, the solid concentration thereof is 30% and 90%, respectively. As for the pretreatment product of the first cellulose-containing biomass, a wet weight of 150 g corresponds to a solid content of 45 g; and, as for the amount of the second cellulose-containing biomass or the pretreatment product thereof added, a solid content of 0.45 to 22.5 g thus corresponds to a wet weight of 0.5 to 25 g.

The pretreatment product of the first cellulose-containing biomass and the second cellulose-containing biomass or the pretreatment product thereof are hydrolyzed using a filamentous fungus-derived cellulase. Examples of the filamentous fungus include microorganisms of the genus *Trichoderma*, the genus *Aspergillus*, the genus *Cellulomonas*, the genus *Chlostridium*, the genus *Streptomyces*, the genus *Humicola*, the genus *Acremonium*, the genus *Irpex*, the genus *Mucor*, and the genus *Talaromyces*. Further, cellulase derived from mutant strains with improved productivity of cellulase by subjecting those microorganisms to mutagenesis using a mutagen, UV irradiation or the like may be used.

Among these filamentous fungi, the genus *Trichoderma* is preferably used because it produces a large amount of enzyme components with a high specific activity in a culture medium in the hydrolysis of cellulose. Specific examples of the cellulase derived from the genus *Trichoderma* include cellulase derived from *Trichoderma reesei* QM9414, *Trichoderma reesei* QM9123, *Trichoderma reesei* RutC-30, *Trichoderma reesei* PC3-7, *Trichoderma reesei* CL-847, *Trichoderma reesei* MCG77, *Trichoderma reesei* MCG80, *Trichoderma viride* QM9123. Of these, cellulase derived from *Trichoderma reesei* is more preferred.

A filamentous fungus-derived cellulase is an enzyme composition having an activity of hydrolyzing cellulose and/or hemicellulose to generate monosaccharides such as glucose or xylose; and preferably contains, as enzyme components, one or more types selected from the group consisting of: cellobiohydrolase, endoglucanase, β-glucosidase, xylanase, and β-xylosidase. Examples of the enzyme component of the cellulase derived from *Trichoderma reesei* include cellobiohydrolase I, cellobiohydrolase II, endoglucanase I, endoglucanase III, β-glucosidase, xylanase, and β-xylosidase; and these plural enzyme components are preferably used because efficient hydrolysis of cellulose and/or hemicellulose can be carried out through concert effects or complementary effects.

Cellobiohydrolase is a general term for enzymes that release cellobiose by hydrolysis of a cellulose chain. The group of enzymes belonging to cellobiohydrolase is described as the EC number: EC3.2.1.91. Cellobiohydrolase I initiates the hydrolysis reaction from the reducing terminal side of the cellulose chain and cellobiohydrolase II does from the non-reducing terminal side.

Endoglucanase is a general term for enzymes characterized by hydrolyzing cellulose from the central portion of a cellulose chain. The group of enzymes belonging to endoglucanase is described as the EC number: EC3.2.1.4.

β-glucosidase is a general term for enzymes characterized by acting on cello oligosaccharides or cellobiose. The group of enzymes belonging to β-glucosidase is described as the EC number: EC3.2.1.21.

Xylanase is a general term for enzymes characterized by acting on hemicellulose or, in particular, xylan. The group of enzymes belonging to xylanase is described as the EC number: EC3.2.1.8.

β-xylosidase is a general term for enzymes characterized by acting on xylooligosaccharides. The group of enzymes belonging to xylosidase is described as the EC number: EC3.2.1.37.

These cellulase components are separated by a known technique such as gel filtration, ion exchange, or two-dimensional electrophoresis and identified by carrying out amino acid sequencing (N-terminal analysis, C-terminal analysis, mass spectrometry) for the component separated, followed by comparison of the result to a database.

In addition, the enzymatic activity of filamentous fungus-derived cellulase can be evaluated based on its hydrolytic activity using, as a substrate, polysaccharides such as crystalline cellulose, carboxymethylcellulose (CMC), cellobiose, xylan, or mannan. A principal enzyme exhibiting the crystalcellulolytic activity is cellobiohydrolase characterized by hydrolyzing cellulose from the terminal portion. A principal enzyme exhibiting the activity of breaking down cellobiose is β-glucosidase. Principal enzymes exhibiting the activity of breaking down CMC are cellobiohydrolase and endoglucanase. Principal enzymes exhibiting the activity of breaking down xylan are xylanase and β-xylosidase. When used herein, the term "principal" is an expression based on a fact that the enzyme is known to be most involved in the breakdown and means that other enzyme components other than this are involved in that breakdown.

Because filamentous fungi produce cellulase in a culture medium, the culture medium as is may be used as a crude enzyme agent; or the group of enzymes may be purified by a known method and formulated to be used as a filamentous fungus-derived cellulase mixture. When the filamentous fungus-derived cellulase is used as one that is purified and formulated, one that is added with substances other than the enzyme such as protease inhibitors, dispersants, dissolution promoters, or stabilizers may be used as a cellulase preparation. Of those, crude enzymes are preferably used. The crude enzyme is derived from the culture supernatant of the medium in which the filamentous fungus is cultured for any period of time, the medium being prepared such that the microorganism produces cellulase. Medium components used are not particularly restricted; and a medium with cellulose being added can be generally used to promote production of cellulase. Then, as the crude enzyme, a culture liquid as is or the supernatant of the culture obtained only by removing *Trichoderma* fungus body is preferably used.

A weight ratio of each enzyme component in the crude enzyme is not particularly restricted. For example, a culture liquid derived from *Trichoderma reesei* contains 50 to 95% by weight cellobiohydrolase; and the remaining components include endoglucanase, β-glucosidase and the like. The genus *Trichoderma* microorganisms produce strong cellulase components in a culture medium. On the other hand, with regard to β-glucosidase, the enzyme is largely kept inside the cell or on the surface layers of the cell and, therefore, the β-glucosidase activity is low in the culture medium. In view this, β-glucosidase from different species or the same species may be further added to the crude enzyme. As the β-glucosidase from different species, β-glucosidase derived from the genus *Aspergillus* can be preferably used. Examples of the β-glucosidase derived from the genus *Aspergillus* include Novozyme 188 which is commercially available from Novozymes A/S. In addition, a culture medium with improved β-glucosidase activity may be used, the culture medium being obtained by introducing a gene to the genus *Trichoderma* microorganism and culturing the genus *Trichoderma* microorganism that is genetically-modified to produce the gene product in the culture medium.

The solid concentration of the pretreatment product of the first cellulose-containing biomass and the second cellulose-containing biomass or the pretreatment product thereof is not particularly restricted and is preferably 1 to 30% by weight. In view of the concentration of sugars generated and handling thereof, it is advantageous to set to such a solid concentration.

The temperature of hydrolysis reaction is not particularly restricted as long as it is in accordance with reaction conditions preferred for the filamentous fungus-derived cellulase and is preferably 30 to 75° C. In particular, when the cellulase derived from the genus *Trichoderma* is used, the temperature is further preferably 40 to 60° C.

Similarly, the pH of hydrolysis reaction is not particularly restricted as long as it is in accordance with reaction conditions preferred for the filamentous fungus-derived cellulase; and is preferably pH 3.0 to 7.0 and further preferably pH 4.0 to 6.0. When the cellulase derived from the genus *Trichoderma* is used as the filamentous fungus-derived cellulase, the optimum reaction pH is 5.0. Further, because changes in the pH takes place in the process of hydrolysis, the reaction is carried out preferably with a buffer being added to a reaction liquid or while the pH is kept constant by using an acid or an alkali.

A period of time for the hydrolysis reaction is preferably two hours to 200 hours. From the viewpoint of generating a sufficient amount of sugars and preventing recovered cellulase from losing its activity, it is advantageous to set the period of time for the hydrolysis reaction in such a range.

Step (3): the step of subjecting the hydrolysate of step (2) to solid-liquid separation to obtain a solution component and a hydrolysis residue and filtering the solution component through an ultrafiltration membrane to recover filamentous fungus-derived cellulase as the retentate and to recover a sugar liquid as the permeate A filamentous fungus-derived cellulase component and a sugar component are contained in a solution component obtained by subjecting the hydrolysate obtained in step (2) to solid-liquid separation; and these can be separated by filtration with an ultrafiltration membrane.

An ultrafiltration membrane is a membrane with a molecular weight cut off of about 500 to 200,000 and is abbreviated as a UF membrane or the like. Further, the pore diameter of the ultrafiltration membrane is so small that it is difficult to measure the fine pore diameter of the membrane surface by an electron microscope or the like; and a value termed as molecular weight cut off, instead of an average fine pore diameter, has been used as an index for the size of pore diameter. The molecular weight cut off refers to one well known as an index representing membrane performance of ultrafiltration membrane, as is described that "a curve obtained by plotting data with the molecular weight of the solute along the horizontal axis and the blocking rate along the vertical axis is called a molecular weight cut off curve; and the molecular weight at which the blocking rate is 90% is called the molecular weight cut off of the membrane." in The Membrane Society of Japan ed., Membrane Experiment Series, Vol. III, Artificial Membrane, edited by Shoji Kimura, Shin-ichi Nakao, Haruhiko Ohya, and Tsutomu Nakagawa (1993 Kyoritsu Shuppan Co., Ltd.), page 92.

In the separation between the filamentous fungus-derived cellulase and the sugar component using an ultrafiltration membrane, the molecular weight cut off is not particularly restricted as long as it allows passage of monosaccharides, namely glucose (molecular weight 180) and xylose (molecular weight 150), which are the major components of sugar liquid, and can block the filamentous fungus-derived cellulase. It is preferred to be a molecular weight cut off of 500 to 100,000. From the viewpoint of ensuring high yield of filamentous fungus-derived cellulase component and separating foreign substances that exhibit actions inhibitory to the enzymatic reaction from the filamentous fungus-derived cellulase component, the molecular weight cut off is more preferably 5,000 to 50,000 and still more preferably 10,000 to 30,000.

As materials of the ultrafiltration membrane, polyether sulfone (PES), polysulfone (PS), polyacrylonitrile (PAN), polyvinylidene difluoride (PVDF), regenerated cellulose, cellulose, cellulose ester, sulfonated polysulfone, sulfonated polyether sulfone, polyolefin, polyvinyl alcohol, polymethylmethacrylate, polyethylene tetrafluoride and the like can be used. Because regenerated cellulose, cellulose, and cellulose ester are subjected to the breakdown by the filamentous fungus-derived cellulase, ultrafiltration membranes with synthetic polymers such as PES or PVDF as a material are preferably used.

As a filtration method with ultrafiltration membrane, dead-end filtration and cross flow filtration are available with cross flow filtration being preferred from the viewpoint of inhibition of membrane fouling. Further, as for a membrane form of the ultrafiltration membrane used, ones in an appropriate form such as a flat membrane type, a spiral type, a tubular type, or a hollow fiber type can be used. Specific examples thereof include G-5 type, G-10 type, G-20 type, G-50 type, PW type, and HWSUF type, which are available from DESAL; HFM-180, HFM-183, HFM-251, HFM-300, HFK-131, HFK-328, MPT-U20, MPS-U20P, and MPS-U20S, which are available from KOCH; SPE1, SPE3, SPE5, SPE10, SPE30, SPV5, SPV50, and SOW30, which are available from Synder; ones corresponding to a molecular weight cut off of 3,000 to 10,000 in Microza (registered trademark) UF series which is manufactured by Asahi Kasei Corporation; and NTR7410 and NTR7450, which are manufactured by Nitto Denko Corporation.

The filamentous fungus-derived cellulase that is recovered in step (2) as the retentate of filtration by ultrafiltration membrane can be reused in the hydrolysis step. The amount of filamentous fungus-derived cellulase used can be decreased by reusing the recovered cellulase to reduce the costs of sugar liquid production. When cellulose-containing biomass is hydrolyzed by using the cellulase recovered, unused filamentous fungus-derived cellulase may be newly added to the cellulase recovered. Because an increase in the amount of the newly-added filamentous fungus-derived cellulase works against the advantage in terms of the cost, it is preferred to add a minimum amount of the unused cellulase to achieve a sufficient yield of sugars.

The sugar liquid recovered as the permeate of filtration by ultrafiltration membrane is one with monosaccharides of glucose and xylose as major components. The sugar liquid is, even without any further treatment, usable as a fermentation raw material in the fermentation step described later; yet a concentration treatment for further increasing the concentration of sugars may be carried out for the purpose of increasing the efficiency of the fermentation step. Examples of the concentration treatment of the sugar liquid can include evaporation concentration, reduced pressure concentration, and membrane concentration; and a concentrated sugar liquid in which sugar components are concentrated can be obtained by a method of filtration by a nanofiltration membrane and/or reverse osmosis membrane, the method requiring less energy consumption, being capable of separating fermentation inhibitors contained in the sugar liquid, and being described in WO 2010/067785.

Microorganisms having an ability to produce chemical substances using the obtained sugar liquid as a fermentation raw material can be cultured to produce various chemical substances. To grow a microorganism as a fermentation raw material herein means proliferation and maintained growth of a microorganism using sugar components or amino sources contained in the sugar liquid as nutrients of the microorganism. Such chemical substances are produced and accumulated as chemical substances inside or outside of the organism in the process of metabolism using the sugar component in the sugar liquid as a carbon source. Specific examples of the chemical substance can include alcohols such as ethanol, 1,3-propanediol, 1,4-butanediol, or glycerol; organic acids such as acetic acid, lactic acid, pyruvic acid, succinic acid, malic acid, itaconic acid, or citric acid; nucleosides such as inosine or guanosine, nucleotides such as inosinic acid or guanylic acid, and amine compounds such as cadaverine. Further, the sugar liquid derived from cellulose can be applied to production of enzymes, antibiotics, recombinant proteins or the like.

EXAMPLES

By way of examples, our methods will be more specifically described below. This disclosure is, however, not limited thereto.

Reference Example 1: Measurement of the Concentration of Proteins

As for the concentration of proteins, a commercially-available protein concentration measurement reagent (Quick Start Bradford protein assay, manufactured by Bio-Rad) was used. To 250 μL of protein concentration measurement reagent that had brought back to room temperature, 5 μL of diluted cellulase solution was added. The mixture was left to stand at room temperature for five minutes and thereafter subjected to measurement of absorbance at 595 nm using a microplate reader (POWERSCAN HT, manufactured by Dainippon Sumitomo Pharma Co., Ltd.). An aqueous solution of bovine serum albumin was used as a standard liquid and the protein concentration of cellulase solution was calculated by referring to a calibration curve.

Reference Example 2: Measurement of the Concentration of Sugars

The concentration of glucose and xylose that were contained in a sugar liquid was quantified in HPLC conditions described below by comparing to a standard sample:
Column: Luna $NH_2$ (manufactured by Phenomenex)
Mobile phase: Milli-Q: acetonitrile=25:75 (flow rate 0.6 mL/min)
Detection method: RI (differential refractive index)
Temperature: 30° C.

Reference Example 3: Method of Measuring Activities of Filamentous Fungus-Derived Cellulase As for activities cellulase, activities of breaking down (1) 4-nitrophenyl-β-D-lactopyranoside (pNP-Lac) and (2) 4-nitrophenyl-β-D-glucopyranoside (pNP-Glc) as the activities of a group of enzymes involved in the breakdown of cellulose, and the activity of breaking down (3) 4-nitrophenyl-β-D-xylopyranoside (pNP-Xyl) as the activity of enzymes involved in the breakdown of xylan which is a major component of hemicellulose are measured and evaluated by the methods shown below. The above (1) to (3) substrates are collectively referred to as pNP-sugars.

To 0.9 mL of 55 mM acetic acid buffer (pH 5.0) that contains each substrate at a concentration of 1.1 mM each, 0.1 mL of enzyme liquid was added and allowed to react at 30° C. (the final concentration of the substrate was 1 mM and the final concentration of the buffer was 50 mM). The reaction time was set to 60 minutes when the substrate was pNP-Lac, 10 minutes for pNP-Glc, and 30 minutes for pNP-Xyl. The reaction was performed for an exact period of time for each; and then 0.1 mL of 2 M aqueous sodium carbonate solution was added to terminate the reaction and the absorbance at 405 nm was measured (ODtest). The absorbance at 405 nm was also measured in the same manner as described above for, as a blank, one prepared by adding, in the order mentioned, 2 M aqueous sodium carbonate solution and the enzyme liquid to the substrate solution (ODblank). The amount of enzyme that generates 1 μmol of 4-nitrophenol for one minute is defined as 1 U in the above reaction system, and an activity value (U/mL) was calculated according to the following formula. The millimolar molecular extinction coefficient of 4-nitrophenol in the above reaction system is 17.2 L/mmol/cm.

The activity of breaking down pNP-Lac(U/mL)={(ODtest−ODblank)×1.1 (mL)×enzyme dilution factor/dilution ratio}/{17.2×60 (minutes)×0.1 (mL)}

The activity of breaking down pNP-Glc(U/mL)={(ODtest−ODblank)×1.1 (mL)×enzyme dilution factor/dilution ratio}/{17.2×10 (minutes)×0.1 (mL)}

The activity of breaking down pNP-Xyl(U/mL)={(ODtest−ODblank)×1.1 (mL)×enzyme dilution factor/dilution ratio}/{17.2×60 (minutes)×0.1 (mL)}

Comparative Example 1: When the First Cellulose-Containing Biomass Alone is Used Step 1: Pretreatment of the First Cellulose-Containing Biomass
Pretreatment 1: Ammonia Treatment of the First Cellulose-Containing Biomass The first cellulose-containing biomass (corncob or rice straw) was put in a small-sized reactor (manufactured by Taiatsu Techno Corporation, TVS-N2 30 ml) and cooled with liquid nitrogen. Ammonia gas was flowed into this reactor and samples were completely immersed in liquid ammonia. The lid of the reactor was closed; and the sample was left to stand at room temperature for about 15 minutes. The treatment was carried out in an oil bath at 150° C. for one hour. After the treatment, the reactor was taken out from the oil bath; and the ammonia gas was immediately discharged in a fume hood and then the inside of the reactor was evacuated to 10 Pa using a vacuum pump to allow the sample to be dried. The pretreatment product of corncob is designated as pretreatment product 1 and pretreatment product of the rice straw was as pretreatment product 2, which were used in the following examples.

Pretreatment 2: Hydrothermal Treatment of the First Cellulose-Containing Biomass The first cellulose-containing biomass (corncob) was immersed in water and subjected, while stirred, to treatment with an autoclave (manufactured by Nitto Kouatsu) at 180° C. for 20 minutes. The pressure at that time was 10 MPa. After the treatment, the resultant was subjected to solid-liquid separation by centrifugation (3,000 G), thereby obtaining a solution component and a solid. The solid was designated as pretreatment product 3 and was used in the following examples.

Pretreatment 3: Dilute Sulfuric Acid Treatment of the First Cellulose-Containing Biomass The first cellulose-containing biomass (corn stover, wheat or barley straw, or bagasse) was suspended in a 2% sulfuric acid aqueous solution to prepare a slurry with a solid concentration of 30%. Such a slurry was subjected to treatment with an autoclave (manufactured by Nitto Kouatsu) at 150° C. for 30 minutes. After the treatment, the resultant was subjected to solid-liquid separation by centrifugation (3,000 g), thereby obtaining a solution component and a solid. The solid obtained from the pretreatment of corn stover was designated as pretreatment product 4; the solid obtained from the pretreatment of wheat or barley straw was as pretreatment product 5; and the solid obtained from the pretreatment of bagasse was as pretreatment product 6, which were used in the following examples.

Step 2: Hydrolysis by Filamentous Fungus-Derived Cellulose

As a filamentous fungus-derived cellulase, a commercially-available cellulase enzyme liquid ("Accellerase DUET," manufactured by Genencor) was used. When the concentration of proteins in the cellulase enzyme liquid was measured according to Reference Example 1, the concentration was 40 g/L.

For the pretreatment product 1 to the pretreatment product 6 which were prepared in step 1, 1.0 g (solid content weight) of each was weighed and suspended in 7.0 mL of water in a 50 mL-centrifuge tube to prepare a slurry. The pH of slurry was adjusted to 4.7 to 5.3 with dilute sulfuric acid or an ammonium solution; and thereafter 0.2 mL of the cellulase enzyme liquid and water were added to the slurry such that the total weight was 10 g, thereby the solid concentration becoming 10%. The resulting mixture was, while rotated, mixed at 50° C. for 24 hours using a hybridization rotator (SN-06BN manufactured by Nissinrika), thereby obtaining a hydrolysate.

Step 3: Recovery of Filamentous Fungus-Derived Cellulase and Sugar Liquid

The hydrolysate of step 2 was subjected to solid-liquid separation by centrifugation (8,000 G, for 10 minutes), thereby obtaining 8 g of solution component and 2 g of hydrolysis residue. The hydrolysis residue was resuspended in 8 mL of water and subjected again to centrifugation (8,000 G, for 10 minutes) to recover a solution component remained in the hydrolysis residue. The recovered solution components were combined and passed through a microfiltration membrane (25 mm GD/X syringe filter, material: PVDF, manufactured by GE Healthcare Japan Corporation) with an a pore size of 0.2 μm to remove fine particles and thereafter filtered using an ultrafiltration membrane (VIVASPIN20, material: PES, manufactured by Sartorius stedim biotech) with a molecular weight cut off of 10,000. The retentate portion was recovered as a recovered cellulase liquid; and the permeate was recovered as a sugar liquid. With regard to the sugar liquid, the concentration of sugar was measured according to Reference Example 2. With regard to the recovered cellulase liquid, the enzymatic activity was measured according to Reference Example 3.

The concentration of sugars is summarized in Table 1 and the ratio of the enzymatic activity of the recovered cellulase liquid to that of input cellulase enzyme liquid, which is regarded as a residual ratio, is in Table 2.

TABLE 1

|  | Sugar concentration (g/L) | |
| --- | --- | --- |
|  | Glucose | Xylose |
| Pretreatment product 1 | 33 | 29 |
| Pretreatment product 2 | 35 | 16 |
| Pretreatment product 3 | 51 | 12 |
| Pretreatment product 4 | 52 | 8 |
| Pretreatment product 5 | 38 | 12 |
| Pretreatment product 6 | 32 | 22 |

TABLE 2

|  | Residual ratio of pNP-sugar breakdown activity (%) | | |
| --- | --- | --- | --- |
|  | pNP-Lac | pNP-Glc | pNP-Xyl |
| Pretreatment product 1 | 22 | 74 | 31 |
| Pretreatment product 2 | 18 | 13 | 9 |
| Pretreatment product 3 | 15 | 9 | 11 |
| Pretreatment product 4 | 16 | 3 | 5 |
| Pretreatment product 5 | 19 | 27 | 13 |
| Pretreatment product 6 | 17 | 35 | 0 |

Example 1: Use of the Second Cellulose-Containing Biomass

To the pretreatment product 1 or the pretreatment product 3 which was used as the first cellulose-containing biomass, any of three types of corn hull, soybean hull, and wheat hull (wheat bran) was added as the second cellulose-containing biomass in step 2 of Comparative Example 1 in an amount of 10% based on the solid content weight of the first cellulose-containing biomass. As a result, a slurry was prepared with a solid concentration of the first cellulose-containing biomass of 10% and a solid concentration of the second cellulose-containing biomass of 1%. Besides what was described above, production of a sugar liquid was carried out in the same manner as described in Comparative Example 1, thereby obtaining a sugar liquid and a recovered cellulase liquid. For the sugar liquid, the concentration of sugars was measured according to Reference Example 2; and for the recovered cellulase liquid, the activity was measured according to Reference Example 3.

Example 2: Use of the Pretreatment Product of the Second Cellulose-Containing Biomass As the second cellulose-containing biomass, a hydrothermal treatment product or an acid treatment product of three types of corn hull, soybean hull, and wheat hull (wheat bran) was used.

The hydrothermal treatment product was obtained by subjecting a slurry of the second cellulose-containing biomass with a solid concentration of 30% to treatment with an autoclave (manufactured by Nitto Koatsu) at 150° C. for 30 minutes.

The acid treatment product was obtained by subjecting a slurry of the second cellulose-containing biomass having a sulfuric acid in 0.5% with a solid concentration of 30% to treatment with an autoclave (manufactured by Nitto Koatsu) at 150° C. for 30 minutes.

Production of a sugar liquid was carried out in the same manner as described in Comparative Example 1 except that the pretreatment product of the second cellulose-containing biomass was added in a amount of 10% based on the solid weight of the first cellulose-containing biomass in step 2 of Comparative Example 1. When the pretreatment product 1 or the pretreatment product 3 was used as the first cellulose-containing biomass, the hydrothermal treatment product or the acid treatment product of any of the second cellulose-containing biomass (corn hull, soybean hull, and wheat hull) was used. When the pretreatment product 2, the pretreatment product 4, the pretreatment product 5, or the pretreatment product 6 was used as the first cellulose-containing biomass, only the acid treatment product of corn hull was used as the second cellulose-containing biomass. For the obtained sugar liquid and recovered cellulase liquid, the concentration of sugars was measured for the sugar liquid according to Reference Example 2; and for the recovered cellulase liquid, the activity was measured according to Reference Example 3.

The concentration of sugars of Examples 1 and 2 is summarized in Tables 3, 4, and 5; and the residual ratio of enzymatic activity is in Table 6, 7, and 8. From the results, the use of the second cellulose-containing biomass improved the yield of sugars and the activity residual ratio of the recovered cellulase liquid to the enzyme that was initially inputted.

TABLE 3

| Cellulose-containing biomass | | | Sugar concentration (g/L) | |
|---|---|---|---|---|
| First | Second | | Glucose | Xylose |
| Pretreatment product 1 | Comparative Example 1 | None | 33 | 29 |
| | Example 1 No treatment | Corn hull | 38 | 32 |
| | | Soybean hull | 34 | 30 |
| | | Wheat hull | 36 | 33 |
| | Example 2 Hydro thermal Treatment | Corn hull | 41 | 35 |
| | | Soybean hull | 38 | 31 |
| | | Wheat hull | 39 | 35 |
| | Acid treatment | Corn hull | 43 | 36 |
| | | Soybean hull | 44 | 32 |
| | | Wheat hull | 42 | 36 |

TABLE 4

| Cellulose-containing biomass | | | Sugar concentration (g/L) | |
|---|---|---|---|---|
| First | Second | | Glucose | Xylose |
| Pretreatment product 3 | Comparative Example 1 | None | 51 | 12 |
| | Example 1 No treatment | Corn hull | 56 | 13 |
| | | Soybean hull | 53 | 13 |
| | | Wheat hull | 54 | 14 |
| | Example 2 Hydro thermal treatment | Corn hull | 59 | 15 |
| | | Soybean hull | 57 | 13 |
| | | Wheat hull | 56 | 14 |
| | Acid treatment | Corn hull | 62 | 18 |
| | | Soybean hull | 62 | 15 |
| | | Wheat hull | 58 | 17 |

TABLE 5

| Cellulose-containing biomass | | | Sugar concentration (g/L) | |
|---|---|---|---|---|
| First | Second | | Glucose | Xylose |
| Pretreatment product 2 | Comparative Example 1 | None | 35 | 16 |
| | Example 2 | Acid treatment Corn hull | 43 | 19 |
| Pretreatment product 4 | Comparative Example 1 | None | 52 | 8 |
| | Example 2 | Acid treatment Corn hull | 59 | 10 |
| Pretreatment product 5 | Comparative Example 1 | None | 38 | 12 |
| | Example 2 | Acid treatment Corn hull | 45 | 14 |
| Pretreatment product 6 | Comparative Example 1 | None | 32 | 22 |
| | Example 2 | Acid treatment Corn hull | 39 | 25 |

TABLE 6

| Cellulose-containing biomass | | | Residual ratio of pNP-sugar breakdown activity (%) | | |
|---|---|---|---|---|---|
| First | Second | | pNP-Lac | pNP-Glc | pNP-Xyl |
| Pretreatment product 1 | Comparative Example 1 | None | 22 | 74 | 31 |
| | Example 1 No treatment | Corn hull | 36 | 85 | 32 |
| | | Soybean hull | 38 | 86 | 39 |
| | | Wheat hull | 32 | 83 | 33 |
| | Example 2 Hydrothermal treatment | Corn hull | 53 | 87 | 38 |
| | | Soybean hull | 49 | 91 | 51 |
| | | Wheat hull | 37 | 88 | 38 |
| | Acid treatment | Corn hull | 61 | 94 | 43 |
| | | Soybean hull | 55 | 98 | 67 |
| | | Wheat hull | 43 | 89 | 45 |

TABLE 7

| Cellulose-containing biomass | | | Residual ratio of pNP-sugar breakdown activity (%) | | |
|---|---|---|---|---|---|
| First | Second | | pNP-Lac | pNP-Glc | pNP-Xyl |
| Pretreatment product 3 | Comparative Example 1 | None | 15 | 9 | 11 |
| | Example 1 | No treatment Corn hull | 18 | 12 | 12 |
| | | Soybean hull | 17 | 12 | 21 |
| | | Wheat hull | 16 | 12 | 13 |
| | Example 2 | Hydrothermal treatment Corn hull | 27 | 25 | 17 |
| | | Soybean hull | 17 | 23 | 37 |
| | | Wheat hull | 18 | 18 | 19 |
| | | Acid treatment Corn hull | 42 | 38 | 27 |
| | | Soybean hull | 28 | 37 | 54 |
| | | Wheat hull | 31 | 25 | 28 |

TABLE 8

| Cellulose-containing biomass | | | Residual ratio of pNP-sugar breakdown activity (%) | | |
|---|---|---|---|---|---|
| First | Second | | pNP-Lac | pNP-Glc | pNP-Xyl |
| Pretreatment product 2 | Comparative Example 1 | None | 18 | 13 | 9 |
| | Example 2 | Acid treatment Corn hull | 29 | 38 | 51 |
| Pretreatment product 4 | Comparative Example 1 | None | 16 | 3 | 5 |
| | Example 2 | Acid treatment Corn hull | 23 | 18 | 11 |
| Pretreatment product 5 | Comparative Example 1 | None | 19 | 27 | 13 |
| | Example 2 | Acid treatment Corn hull | 28 | 55 | 57 |
| Pretreatment product 6 | Comparative Example 1 | None | 17 | 35 | 0 |
| | Example 2 | Acid treatment Corn hull | 34 | 65 | 48 |

Example 3: Influence of the Amount of the Second Cellulose-Containing Biomass Added The acid treatment product of corn hull was used as the second cellulose-containing biomass in step 2 of Comparative Example 1 and added in an amount of 1 to 50% based on the solid content weight of the pretreatment product 3 of the first cellulose-containing biomass (the hydrothermal treated corncob). Besides what was described above, production of a sugar liquid was carried out in the same manner as described in Comparative Example 1, thereby obtaining a sugar liquid and a recovered cellulase liquid. For the sugar liquid, the concentration of sugars was measured according to Reference Example 2; and for the recovered cellulase liquid, the activity was measured according to Reference Example 3. The concentration of sugars is summarized in Tables 9; and the residual ratio of enzymatic activity is in Table 10.

From the results, the larger amount of the second cellulose-containing biomass added, the more the sugar yield increased. The activity residual ratio of the recovered cellulase liquid for the initially-inputted enzyme reached the maximum when the second cellulose-containing biomass was added in an amount of 10% or more based on the solid content weight of the first cellulose-containing biomass pretreatment product.

TABLE 9

| Cellulose-containing biomass | | Sugar concentration (g/L) | |
|---|---|---|---|
| First | Second | Glucose | Xylose |
| Pretreatment product 3 | None (Comparative Example 1) | 51 | 12 |
| | Corn hull 1% | 53 | 13 |

TABLE 9-continued

| Cellulose-containing biomass | | Sugar concentration (g/L) | |
|---|---|---|---|
| First | Second | Glucose | Xylose |
| | 5% | 59 | 15 |
| | 10% (Example 2) | 62 | 18 |
| | 20% | 67 | 20 |
| | 30% | 69 | 21 |
| | 50% | 72 | 22 |

TABLE 10

| Cellulose-containing biomass | | | Residual ratio of pNP-sugar breakdown activity (%) | | |
|---|---|---|---|---|---|
| First | Second | | pNP-Lac | pNP-Glc | pNP-Xyl |
| Pretreatment product 3 | None (Comparative Example 1) | | 15 | 9 | 11 |
| | Corn hull | 1% | 27 | 22 | 18 |
| | | 5% | 35 | 31 | 24 |
| | | 10% (Example 2) | 42 | 38 | 27 |
| | | 20% | 42 | 39 | 28 |
| | | 30% | 43 | 41 | 27 |
| | | 50% | 42 | 40 | 28 |

Example 4: Fermentative Production of Lactic Acid Using Sugar Liquid Derived from Cellulose-Containing Biomass as a Fermentation Raw Material

*Lactococcus lactis* JCM7638 strain was subjected to static culture at a temperature of 37° C. for 24 hours using, as fermentation raw materials, the sugar liquid produced in Comparative Example 1 (sugar liquid 1) using the pretreatment product 3 (hydrothermal treated corncob) as the first cellulose-containing biomass pretreatment product, and the sugar liquid produced using corn hull that had been subjected to the acid treatment as the second cellulose-containing biomass in Example 2 (sugar liquid 2). The concentration of L-lactic acid contained in the culture medium was analyzed in the conditions below:

Column: Shim-Pack SPR-H (manufactured by Shimadzu Corporation)
Mobile phase A: 5 mM p-toluenesulfonic acid (flow rate 0.8 mL/min)
Mobile phase B: 5 mM p-toluenesulfonic acid, 20 mM bis-Tris, 0.1 mM EDTA.2Na (flow rate 0.8 mL/min)
Detection method: electrical conductivity
Temperature: 45° C.

From the results of the above analysis, it was, as shown in Table 11, confirmed that L-lactic acid was able to be produced by lactic acid fermentation with any of the sugar liquids as the fermentation raw material. It turned out that the sugar liquid produced by our methods exhibited an excellent yield of lactic acid fermentation.

TABLE 11

|  | Sugar liquid 1 | Sugar liquid 2 |
|---|---|---|
| L-lactic acid concentration (g/L) | 10 | 16 |

Our methods of producing a sugar liquid can be used to produce a sugar liquid that serves as a fermentation raw material from biomass that contains cellulose. In addition, the sugar liquid can be used as a fermentation raw material for various chemical substances.

The invention claimed is:

1. A method of producing a sugar liquid comprising steps (1) to (3):
    Step (1): providing a pretreatment product of a first cellulose-containing biomass;
    Step (2): adding a second cellulose-containing biomass or a pretreatment product thereof in an amount of 1 to 50% based on the solid content weight of said first cellulose-containing biomass pretreatment product of step (1), and carrying out hydrolysis by a filamentous fungus-derived cellulase, wherein said second cellulose-containing biomass of step (2) is a grain hull comprising the outermost epidermis of the grain kernel; and
    Step (3): subjecting a hydrolysate of the step (2) to solid-liquid separation to obtain a solution component and a hydrolysis residue, and filtering said solution component through an ultrafiltration membrane to recover said filamentous fungus-derived cellulase as a retentate and recover a sugar liquid as a permeate,
    wherein the plant species or plant parts of said first cellulose-containing biomass are different from those of said second cellulose-containing biomass.

2. The method according to claim 1, wherein said pretreatment product of said second cellulose-containing biomass of step (2) is a pretreatment product obtained by subjecting said second cellulose-containing biomass to a hydrothermal treatment and/or an acid treatment.

3. The method according to claim 2, wherein said second cellulose-containing biomass of step (2) is one or more biomasses selected from the group consisting of a corn hull, a soybean hull, and a wheat hull.

4. The method according to claim 2, wherein said first cellulose-containing biomass of step (1) is a herbaceous biomass or a woody biomass.

5. The method according to claim 2, wherein the first cellulose-containing biomass of step (1) is one or more biomasses selected from the group consisting of corn stover, a corncob, rice straw, wheat straw, barley straw, and bagasse.

6. The method according to claim 2, wherein said pretreatment product of said first cellulose-containing biomass of step (1) is one pretreated by one or more methods selected from the group consisting of an acid treatment, an alkali treatment, a hydrothermal treatment, a subcritical water treatment, a pulverizing treatment, and a steaming treatment.

7. The method according to claim 1, wherein said second cellulose-containing biomass of step (2) is one or more biomasses selected from the group consisting of a corn hull, a soybean hull, and a wheat hull.

8. The method according to claim 7, wherein said first cellulose-containing biomass of step (1) is a herbaceous biomass or a woody biomass.

9. The method according to claim 7, wherein the first cellulose-containing biomass of step (1) is one or more biomasses selected from the group consisting of corn stover, a corncob, rice straw, wheat straw, barley straw, and bagasse.

10. The method according to claim 1, wherein said first cellulose-containing biomass of step (1) is a herbaceous biomass or a woody biomass.

11. The method according to claim 10, wherein the first cellulose-containing biomass of step (1) is one or more biomasses selected from the group consisting of corn stover, a corncob, rice straw, wheat straw, barley straw, and bagasse.

12. The method according to claim 1, wherein the first cellulose-containing biomass of step (1) is one or more biomasses selected from the group consisting of corn stover, a corncob, rice straw, wheat straw, barley straw, and bagasse.

13. The method according to claim 1, wherein said pretreatment product of said first cellulose-containing biomass of step (1) is one pretreated by one or more methods selected from the group consisting of an acid treatment, an alkali treatment, a hydrothermal treatment, a subcritical water treatment, a pulverizing treatment, and a steaming treatment.

14. The method according to claim 1, wherein said grain hull is obtained from at least one selected from Poaceae crops and Fabaceae crops.

15. The method according to claim 1, wherein in Step (2) the second cellulose-containing biomass or pretreatment product thereof is added in an amount of 10 to 50% based on the solid content weight of said first cellulose-containing biomass pretreatment product of step (1).

16. A method of producing a chemical substance comprising producing a sugar liquid by said method according to claim 1; and culturing a microorganism using the sugar liquid obtained in said step of producing the sugar liquid as a fermentation raw material.

* * * * *